US006268501B1

(12) United States Patent
Kiel

(10) Patent No.: US 6,268,501 B1
(45) Date of Patent: Jul. 31, 2001

(54) PROCESS FOR THE PREPARATION OF HYDROXYETHYLCYCLOHEXANES AND HYDROXYETHYLPIPERIDINES

(75) Inventor: Wolfgang Kiel, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/441,595

(22) Filed: Nov. 17, 1999

(30) Foreign Application Priority Data

Nov. 23, 1998 (DE) .............................................. 198 53 858

(51) Int. Cl.$^7$ .................................................. C07D 211/12
(52) U.S. Cl. ................................................................ 546/185
(58) Field of Search ............................................... 546/185

(56) References Cited

FOREIGN PATENT DOCUMENTS

| 2132547 | 1/1973 | (DE) . |
| 2550716 | 4/1977 | (DE) . |
| 2071653 | 9/1981 | (GB) . |

OTHER PUBLICATIONS

Burtner, Robert R. et al: "Antispasmodics III. Diarylacetic Acid Esters of Some Pyridyl and Piperidyl Alkanols", Journal of the American Chemical Society, Bd 69, 1947, Seiten 630–633, XP002134816, American Chemical Society, Washington, DC, US, ISSN: 0002–7863, Seite 630–Seite 631.

Patent Abstract of Japan, C–625, Aug. 14, 1989, vol. 13, No. 362, JP 1–121226, Production of 2–Cyclohexylethanol.

Patent Abstract of Japan, JP 08187432 A, Jul. 23, 1996, Hydrogeneration Catalyst and Reaction Using the Same.

Patent Abstract of Japan, C–277, Apr. 19, 1985, vol. 9, No. 91, JP 59–225134 A, Preparation of 1–(1–Hydroxyethyl)–4–Isobutylcyclohexane.

Database WPI, Section Ch, Week 197706, Derwent Publications Ltd., London, GB; AN 1977–006727, XP002134818 & RO 61 609 A (Terapia Intr Medica), Jul. 31, 1976, Zusammenfassung.

Database WPI, Section Ch, Week 199205, Derwent Publications Ltd., London GB; AN 1992–037688, XP002134817 & JP 03 284640 A (Sumitomo Chem Co Ltd), Dec. 16, 1991, Zusammenfassung.

Vasil'Ev A. A. et al: "Compounds With A Herbal Odor II. Cis–1–(2–Hydroxyethyl)–2–Ethylcyclo–alkanes and Their Analogs", Journal of Organic Chemistry of the USSR (Zhurnal Organicheskoi Khimii), Bd. 27, Nr. 2, 1991, Seiten 273–278, XP002134815, Consultants Bureau, New York, US, Seite 278.

*Primary Examiner*—Zinna Northington Davis
(74) *Attorney, Agent, or Firm*—Joseph C. Gil; Diderico van Eyl

(57) ABSTRACT

Hydroxyethylcyclohexanes which can optionally contain a nitrogen atom in the cyclohexane ring are obtained in a particularly selective manner by catalytic hydrogenation of the corresponding hydroxyethylbenzene or hydroxyethylpyridines when ruthenium which has been treated before use with a reducing agent is used as catalyst.

10 Claims, No Drawings

PROCESS FOR THE PREPARATION OF HYDROXYETHYLCYCLOHEXANES AND HYDROXYETHYLPIPERIDINES

BACKGROUND OF THE INVENTION

The present invention relates to a process for the preparation of hydroxyethylcyclohexanes which can optionally contain a nitrogen atom in the hexane ring by catalytic hydrogenation of the corresponding hydroxyethylbenzenes or hydroxyethylpyridines.

Hydroxyethylcyclohexanes and hydroxyethylpiperidines are intermediates for the preparation of pharmaceuticals, fragrances and insect repellents.

When hydroxyethylcyclohexanes and hydroxyethylpiperidines are prepared using customary hydrogenation catalysts such as Raney nickel or rhodium and/or in polar solvents by hydrogenation of the corresponding hydroxyethylbenzenes or hydroxyethylpyridines, secondary reactions take place to a considerable extent, which lead to the formation of undesired byproducts. There is therefore a need for a process which can be used to prepare hydroxyethylcyclohexanes which can optionally contain a nitrogen atom in the cyclohexane ring in good selectivities of, for example, greater than 95%.

We have now found a process for the preparation of hydroxyethylcyclohexanes which can optionally contain a nitrogen atom in the cyclohexane ring by catalytic hydrogenation of the corresponding hydroxyethylbenzenes or hydroxyethylpyridines which is characterized in that ruthenium which has been treated before use with a reducing agent is used as catalysts.

DESCRIPTION OF THE INVENTION

According to the invention, it is, for example, possible to use hydroxyethylbenzenes and hydroxyethylpyridines of the formula (1)

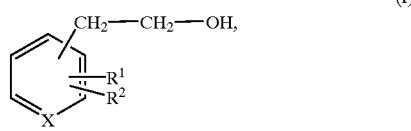

(I)

in which

X is CH or N and $R^1$ and $R^2$ independently of one another are each hydrogen, hydroxyl, amino, $C_1$–$C_{10}$-alkyl, $C_3$–$C_6$-cycloalkyl, $C_6$–$C_{10}$-aryl, $C_7$–$C_{12}$-aralkyl, $C_1$–$C_{10}$-alkoxy or $C_3$–$C_6$-cycloalkoxy, and to obtain hydroxyethylcyclohexanes which can optionally contain a nitrogen atom in the cyclohexane ring and correspond to the formula (II)

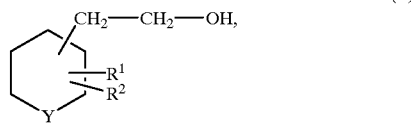

(II)

in which

Y is $CH_2$ or NH and $R^1$ and $R^2$ are defined for formula (I).

In the formulae (I) and (II), $R^1$ and $R^2$ are preferably independently of one another hydrogen, $C_1$–$C_4$-alkyl, benzyl or $C_1$–$C_4$-alkoxy. $R^1$ and $R^2$ are particularly preferably hydrogen.

In formula (I), X is preferably N. Correspondingly, in formula (II), Y is preferably NH.

In the formulae (I) and (II), the hydroxyethyl group is preferably in the 2-position relative to X or Y. $R^1$ and $R^2$ are preferably in the 3-, 4-, 5- and/or 6-position relative to X or Y.

Particular preference is given to using 2-(2-hydroxyethyl)-pyridine or hydroxyethylbenzene in the process according to the invention and to preparing 2-(2-hydroxyethyl-piperidine or hydroxyethylcyclohexane.

Preferred ruthenium catalysts are those which comprise metallic ruthenium (i.e. ruthenium in oxidation state ±0) on a support. The ruthenium content of such supported catalysts can, for example, be from 0.5 to 15% by weight, preferably from 1 to 10% by weight.

The treatment of the ruthenium with a reducing agent prior to its use in the process according to the invention can for example be carried out with hydrogen at an elevated temperature or with another suitable reducing agent, such as for example hydrazine. If the treatment is carried out with hydrogen, pressures of for example 120 to 250 bar and temperatures of 120 to 250° C. can be used. 150 to 220 bar and 150 to 220° C. are preferred. The treatment with another suitable reducing agent, such as for example hydrazine, can be carried out in the presence of a solvent at pressures of for example normal pressure to 5 bar and temperatures of for example 20 to 80° C. Suitable solvents are for example water and organic solvents such as isopropanol and methylcyclohexane as well as acids such as sulphuric acid or acetic acid. Already prepared hydroxyethylcyclohexane, which can optionally contain a nitrogen atom in the cyclohexane ring, can also be used as the solvent if it is liquid under the treatment conditions. Treatment with hydrogen is preferred.

Examples of support materials for the supported catalysts are charcoals, aluminium oxides or silicas. It is also possible to use other known support materials for metal catalysts.

Supported catalysts which are suitable for the process according to the invention, optionally after treatment with a reducing agent, are available commercially.

In the discontinuous procedure, it is possible to use, for example from 0.01 to 10% by weight of ruthenium catalyst (taking only Ru metal into account and based on hydroxyethylbenzene or hydroxyethylpyridine used). This amount is preferably from 0.1 to 2.5% by weight.

After having been separated off from the reaction mixture, the catalysts can be used again in the process according to the invention. It is also possible to carry out the process according to the invention continuously.

The process according to the invention can optionally be carried out in the presence of solvents.

Suitable solvents are a very wide variety of alkanes which can. for example, be straight-chain, branched or cyclic and are liquid under the reaction conditions. Preference is given to alkanes which have a boiling point above 70° C. at atmospheric pressure, in particular straight-chain and branched acyclic $C_7$–$C_{18}$-alkanes, unsubstituted cyclic $C_6$–$C_{10}$-alkanes and $C_5$–$C_{10}$-alkanes substituted by straight-chain or branched $C_1$–$C_{10}$-alkyl groups. Particularly preferred solvents are isooctane, cyclohexane and methylcyclohexane, in particular methylcyclohexane. It is also possible to use mixtures of various alkanes.

Based on 100 g of hydroxyethylbenzene or hydroxyethylpyridine used, it is possible to use, for example, from 10 to 1000 ml of solvent. This amount is preferably from 20 to 100 ml.

The hydrogenation according to the invention can, for example. be carried out at temperatures in the range from 50 to 250° C. and hydrogen pressures of from 5 to 200 bar. Preference is given to temperatures in the range from 80 to 220° C. and hydrogen pressures from 50 to 180 bar.

It is possible to carry out the process according to the invention, for example, by firstly introducing the hydroxyethylbenzene or hydroxyethylpyridine used, optionally together with the solvent, into a pressurized vessel and rendering the pressurized vessel inert, for example by flushing with nitrogen. Separately from this, the catalyst has preferably been pretreated with hydrogen or another suitable reducing agent. The catalyst, preferably suspended in the same solvent as is already present in the pressurized vessel, is added to the pressurized vessel, which is then heated to the reaction temperature, and hydrogen is injected. The reaction is generally complete after from 30 minutes to 10 hours (hydrogen is no longer absorbed). The mixture present can then be worked up by firstly cooling it, releasing the pressure, then separating off the catalyst and isolating the hydroxyethylcyclohexane or hydroxyethylpiperidine prepared, for example by distillation.

Other ways of carrying out the process according to the invention are also possible, in particular including those carried out continuously.

Using the process according to the invention it is possible to prepare hydroxethylcyclohexane and hydroxyethylpiperidines in high yields and with very high selectivities. The selectivities, based on reacted starting material, are generally greater than 95%, and frequently greater than 98%. The service lives of the catalysts are also long in the process according to the invention.

The invention is further described in the following illustrative examples in which all parts and percentages are by weight unless otherwise indicated.

EXAMPLES

Example 1

150 g of 2-(2-hydroxyethyl)-pyridine were mixed with 50 g of methylcyclohexane and introduced into a 0.7 l stirred autoclave. The autoclave was then rendered inert 3 times with 5 bar of $N_2$. 10 g of a catalyst comprising 5% by weight of ruthenium on charcoal, suspended in 50 ml of methylcyclohexane, were then pumped in. The catalyst had previously been treated with $H_2$ at 200° C. and 200 bar. The mixture was hydrogenated at 150° C. and an $H_2$ pressure of 80 bar. The hydrogenation time was 5 hours.

A crude mixture having the following composition (GC) was obtained:

2-(2-hydroxyethyl)-piperidine: 98.6%

2-ethylpiperidine: 0.4% other ethylpiperidines: 0.5%

Example 2

The procedure was as in Example 1, but 10 g of a catalyst were used which comprised 5% by weight of ruthenium on aluminium oxide. The crude mixture obtained comprised 96.6% (GC) of 2-(2-hydroxyethyl)-piperidine.

Example 3 (as comparison)

The procedure was as in Example 1, but 3 g of Raney nickel were used as catalyst. The crude mixture obtained comprised (GC):

2-(2-hydroxyethyl)-piperidine: 48.6% methylpiperidines: 19.9% hydroxyethyl-ethylpiperidines: 19.3%

Example 4 (as comparison)

The procedure was as in Example 1, but 10 g of a catalyst comprising 5% by weight of rhodium on carbon were used. The crude mixture obtained comprised (GC):

2-(2-hydroxyethyl)-piperidine: 79.7% hydroxyethylpyridine: 14.9% ethylpiperidines: 3.8%

Example 5

150 g hydroxyethylbenzene were mixed with 50 g of methylcyclohexane and introduced into a 0.7 l stirred autoclave. The autoclave was then rendered inert 3 times with 5 bar of $N_2$. 5 g of a catalyst comprising 5% by weight of ruthenium on carbon, suspended in 50 ml of methylcyclohexane, were then pumped in. The catalyst had previously been treated with $H_2$ at 200° C. and 200 bar. The mixture was hydrogenated at 100° C. and an $H_2$ pressure of 150 bar. The hydrogenation time was 45 times.

A crude mixture having the following composition (GC) was obtained:

hydroxyethylcyclohexane: 99.3% ethylcyclohexane: 0.3

Example 6 (as comparison)

The procedure was as in Example 1, but instead of each 50 g of methylcyclohexane, 100 g of methanol were used in each case. The crude mixture obtained comprised (GC):

2-(2-hydroxyethyl)-piperidine: 81.5% methylpiperidine: 6.3% ethylpiperidine: 4.4% hydroxyethyl-ethylpiperidine: 6.6% unknown substances: remainder

Although the present invention has been described in detail with reference to certain preferred versions thereof, other variations are possible. Therefore, the spirit and scope of the appended claims should not be limited to the description of the versions contained therein.

What is claimed is:

1. A process for the preparation of a hydroxyethylcyclohexane that contains a nitrogen atom in the cyclohexane ring by catalytic hydrogenation of the corresponding hydroxyethyl pyridine, wherein ruthenium which has been treated before use with a reducing agent is used as catalyst.

2. A process according to claim 1, wherein a hydroxyethylpyridine of the formula (I)

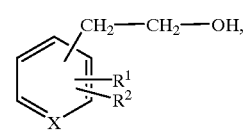

wherein

X is N and $R^1$ and $R^2$ independently of one another are each hydrogen, hydroxyl, amino, $C_1$–$C_{10}$-alkyl, $C_3$–$C_6$-cycloalkyl, $C_6$–$C_{10}$-aryl, $C_7$–$C_{12}$-aralkyl, $C_1$–$C_{10}$-alkoxy or $C_3$–$C_6$-cycloalkoxy, is used and a hydroxyethylcyclohexane that contains a nitrogen atom in the cyclohexane ring and corresponds to the formula (II)

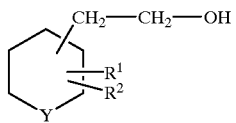

wherein
Y is NH and
$R^1$ and $R^2$ are as defined above, is obtained.

3. A process according to claim 1, wherein the ruthenium catalyst used comprises a metallic ruthenium on a support.

4. A process according to claim 1, wherein a ruthenium-containing supported catalyst is used which, prior to its use, has been treated with hydrogen or another reducing agent at an elevated temperature.

5. A process according to claim 1, wherein the pretreatment of the ruthenium is carried out with hydrogen at a temperature ranging from 120 to 250° C. and a pressure ranging from 120 to 250 bar.

6. A process according to claim 1, wherein a ruthenium-containing supported catalyst which contains, as a support material, charcoals, aluminum oxides or silicas is used.

7. A process according to claim 1, wherein the process is practiced continuously and from 0.01 to 10% by weight of ruthenium catalyst (taking only Ru metal into account), based on hydroxyethylpyridine used, is used.

8. A process according to claim 1, wherein the process is carried out in a solvent which is an alkane which has a boiling point above 70° C. at atmospheric pressure.

9. A process according to claim 8, wherein the alkane used comprises a component selected from the group consisting of isooctane, cyclohexane and methylcyclohexane.

10. A process according to claim 1, wherein the hydrogenation is carried out at a temperature ranging from 50 to 250° C. and a hydrogen pressure ranging from 5 to 200 bar.

* * * * *